United States Patent [19]
Gebhardt

[11] Patent Number: 5,197,480
[45] Date of Patent: Mar. 30, 1993

[54] SYSTEM AND METHOD FOR MONITORING HEART TRANSPLANT REJECTION

[75] Inventor: Ursala Gebhardt, Huissen, Netherlands

[73] Assignee: Vitatron Medical, B.V., Dieren, Netherlands

[21] Appl. No.: 535,336

[22] Filed: Jun. 8, 1990

[51] Int. Cl.⁵ .......................................... A61B 5/0452
[52] U.S. Cl. ..................................... 128/697; 128/702
[58] Field of Search ................. 128/696, 697, 702-704, 128/419 PG, 419 PT

[56] References Cited

U.S. PATENT DOCUMENTS

| | | | |
|---|---|---|---|
| 3,572,321 | 3/1971 | Bloomfield et al. | 128/704 |
| 3,593,705 | 7/1971 | Thomas et al. | 128/703 |
| 3,606,882 | 9/1971 | Abe et al. | 128/704 |
| 4,305,396 | 12/1981 | Witikampf et al. | 128/419 PG |
| 4,759,366 | 7/1988 | Callaghan | 128/704 |
| 4,759,367 | 7/1988 | Callaghan | 128/704 |
| 4,905,707 | 3/1990 | Davies et al. | 128/702 |

Primary Examiner—William E. Kamm
Attorney, Agent, or Firm—Woodcock Washburn Kurtz Mackiewicz & Norris

[57] ABSTRACT

A pacemaker system and method for predicting cardiac allograft rejection noninvasively through the analysis of the T-wave amplitudes of evoked heartbeats. A pacemaker suitable for detecting the T-wave portions of heartbeat signals, such as the Rhythmyx pacemaker, is utilized for providing T-wave information, preferably the amplitude of the T-wave, which information is analyzed for determining a trend indicative of rejection. A decrease, or diminution of evoked T-wave amplitude indicates rejection, and can be used for appropriate follow-up treatment.

20 Claims, 4 Drawing Sheets

SYSTEM AND METHOD FOR MONITORING HEART TRANSPLANT REJECTION

FIELD OF THE INVENTION

This invention relates to medical systems and methods for noninvasively monitoring a transplanted heart to diagnose cardiac allograft rejection.

BACKGROUND OF THE INVENTION

It is well known that following human heart transplantation there is danger of rejection of the new heart by the host patient. Such rejection, referred to as cardiac allograft rejection, has been widely studied and discussed in the medical literature. While techniques dealing with, i.e. treating such rejection, have advanced greatly, there still remains a need for accurate, noninvasive, safe and relatively simple diagnosis of such rejection.

One technique for determining the condition of the transplanted heart is to perform a biopsy. However, such an invasive technique is clearly not desirable, and there is a substantial need for an accurate and reliable noninvasive means of diagnosis.

The depolarization phase (QRS) of the surface electrocardiogram has been determined to be a sensitive indicator of myocardial damage, but has proved disappointing in the diagnosis of cardiac allograft rejection. The prior art has employed an implanted lead and an implanted pacemaker in an attempt to predict rejection based upon the amplitude of the depolarization (QRS) wave, but concluded that depolarization wave amplitude is not a reliable indicator of rejection. In this prior scheme, the depolarization wave data was transmitted by telemetry from the pacemaker to an external programmer/transceiver in real time, and then recorded with an EKG recorder.

The inventor of the instant application has discovered that amplitude of the repolarization wave (T-wave), as well as other characteristics of the heartbeat signal, including characteristics of the QRS and T-waves, can, in fact, be employed to predict rejection, as well as to indicate the need for drug treatment or other therapy not necessarily related to heart transplantation. It is believed by the inventor that, in the prior art attempt described above, either degradation of the depolarization wave data during transmission by the pacemaker (as a result of the real time transmission of raw data), or pacemaker inadequacies such as lack of sensitivity, or both, resulted in failure to appreciate the phenomena and hence an erroneous conclusion.

The present invention addresses the acute need for an improved noninvasive technique for both diagnosing rejection of a transplanted heart in a human patient, as well as indicating the need for drug treatment or other therapy not necessarily related to heart transplantation.

Summary of the Invention

It is one object of this invention to provide a system and method for noninvasive diagnosis of a heart transplant recipient's rejection of the transplanted heart, and particularly a system and method for providing a reliable early indication of the onset of rejection so treatment can be anticipated and properly administered. In accordance with this object, there is provided a system and method applicable to a patient who has recently received a transplanted heart for at least periodically pacing the heart with an implanted lead to evoke a heartbeat, sensing and obtaining with the implanted lead heartbeat signals (whether spontaneous or evoked), analyzing a characteristic of the evoked heartbeat signals (such as, but not limited to, the T-wave amplitude) to determine a trend, or direction of change of the characteristic with time, and treating the patient when the characteristic trend or direction of the change of the characteristic with time indicates rejection or onset of rejection.

Other objects of the invention include operating a control system in accordance with the characteristic trend or direction of the change of the characteristic with time. These other objects will become evident hereinafter.

DETAILED DESCRIPTION OF THE PREFERRED EMBODIMENTS

Figure 1:
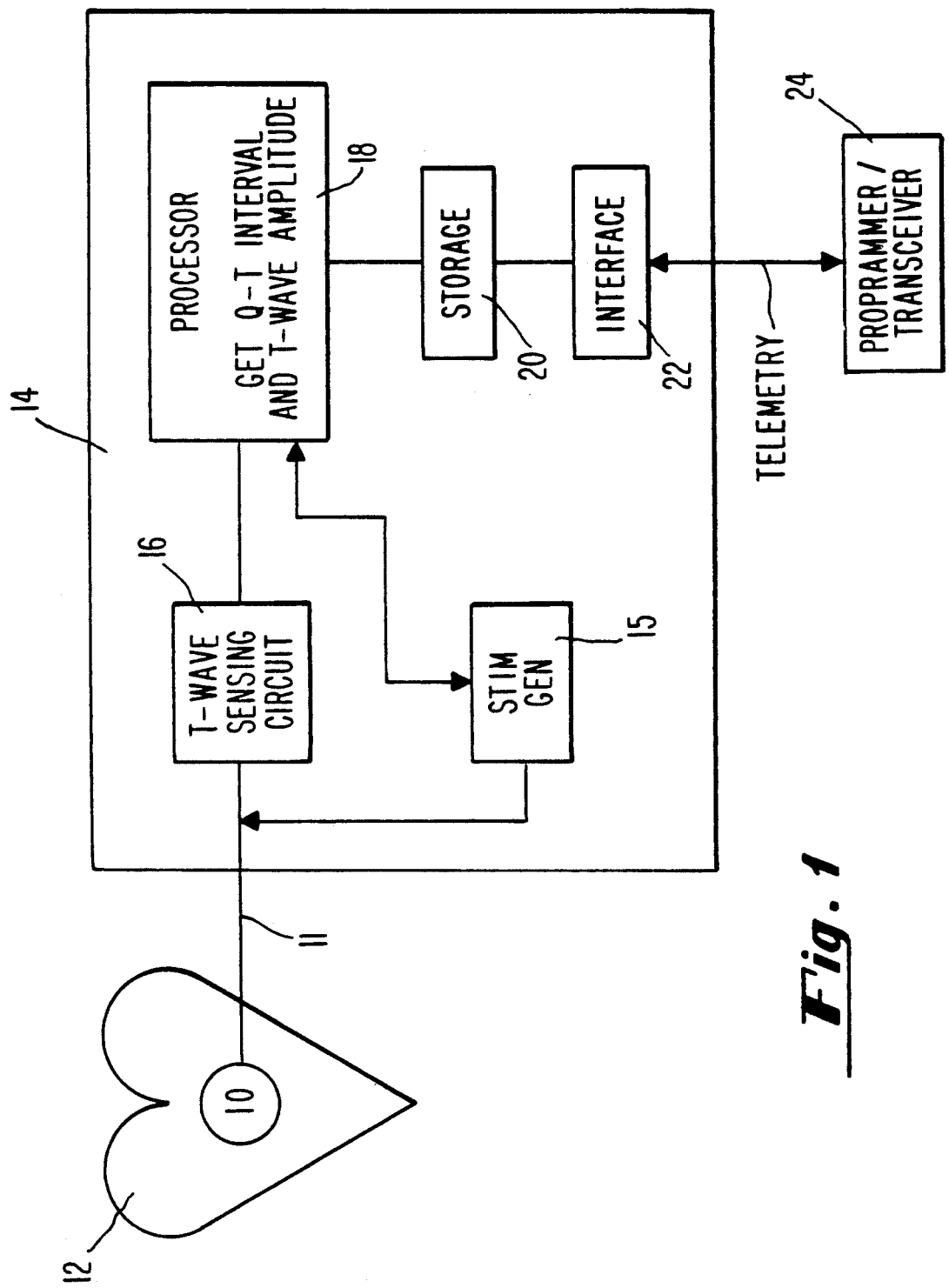
FIG. 1 is block diagram showing one embodiment of a system for practicing the present invention.

Referring to FIG. 1, there is shown a simplified block diagram of one system for noninvasively diagnosing the presence or onset of cardiac allograft rejection according to the invention. Electrodes indicated schematically at 10 are coupled to the heart, as indicated schematically at 12, by a lead 11. Preferably an implanted lead, such as an epicardial or endocardial electrode system, is used for sensing the heartbeat. The intracardiac EKG, or heartbeat signals, are connected to a pacemaker 14. A suitable pacemaker used in the practice of this invention is the Rhythmyx pacemaker, manufactured by the assignee of this application. The Rhythmyx is a commercially available rate-adjustable pacemaker which controls pacing rate as a function of the Q-T interval. For this purpose, the Rhythmyx pacemaker has circuitry for accurately sensing the T-wave or repolarization portion of the heartbeat signal, so as to be able to obtain a periodic measurement of the time interval between a stimulated ventricular event (stimulus) and the following T-wave. See U.S. Pat. Nos. 4,228,803, 4,305,396, 4,373,531 assigned to the assignee of this application, which are incorporated by reference. In the embodiment illustrated in FIG. 1, the pacemaker 14 is implanted within the patient. Outputs from stimulus generator 15 are connected to processor 18 to enable obtaining the Q-T interval, and timing signals from processor 18 are coupled to stimulus generator 15 to trigger output stimulus pulses when the pacemaker escape interval has been timed out, in a known manner. As shown, the T-wave signals are sensed within the pacemaker 14 by T-wave sensing circuitry 16. The sensed T-waves are coupled to processing circuitry 18 within the pacemaker for determining the Q-T interval. The processing circuitry 18 is suitably modified to also determine the amplitude of detected T-waves. Alternatively, the sensing circuitry 16 may be modified to o determine the amplitude of the T-waves and provide this information to processing means 18 for storage in storage circuitry 20 for purposes to be described herein. The storage circuitry 20 may also store other historical data associated with the heart such as detected Q-T intervals, as well as operating parameters for the pacemaker, in well known fashion. Circuitry 22 within the pacemaker 14 provides a telemetry interface between the pacemaker 14 and an external programmer/transceiver 24.

Programmer/transceiver 24 bidirectionally communicates with the pacemaker 14 in well known fashion. At selected or preselected intervals, the programmer/transceiver 24 is employed to obtain the T-wave amplitude data or other data stored in the pacemaker 14 for analysis as described herein. The T-wave amplitude data may be output from the programmer/transceiver 24 to any suitable external device (not shown) such as a video terminal recorder, data storage, etc. for analysis. The T-wave amplitude information may also be compiled, averaged, etc. over any desired period of time by the external device.

Figure 2:
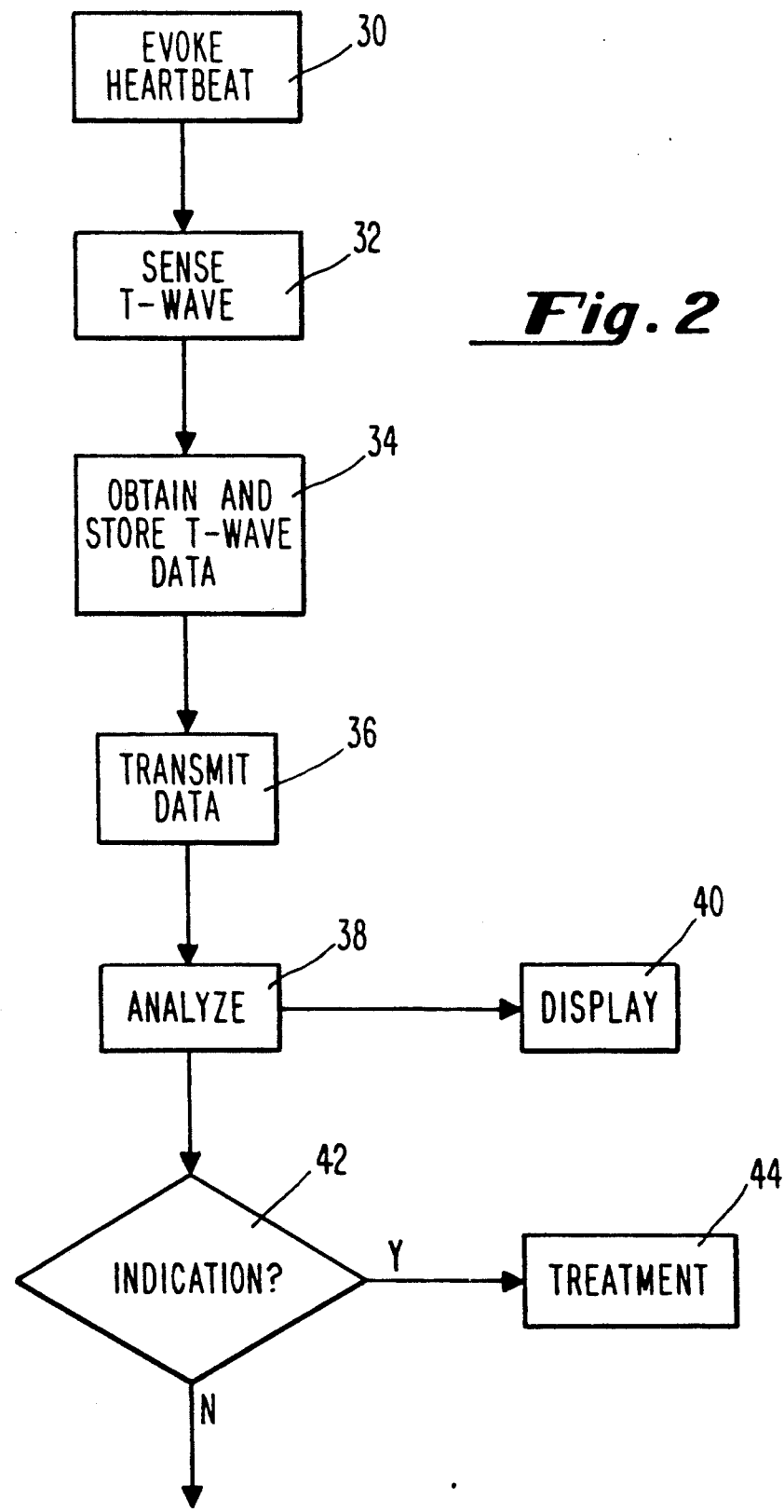
FIG. 2 is a simplified flow chart indicating a method for employing the system of FIG. 1.

FIG. 2 illustrates one method of employing the system of FIG. 1. The method is carried out by evoking the heartbeat with a suitable pacemaker pulse generator as indicated at block 30. The T-wave is then sensed as indicated at 32, and the amplitude data (or data indicative of one or more of the other characteristics described below) is obtained and stored at 34. The amplitude data (and/or other data) is transmitted from the pacemaker 14 to the programmer/transceiver 24 at 36 when required, upon request. The data is then analyzed at 38. The analysis step may include manipulation of the amplitude data, e.g. averaging or the like. The T-wave amplitude data may be displayed, e.g., on a CRT, recorder, etc. as shown at 40. At block 42 it is determined whether the T-wave data is significant in terms of providing an indication of whether or not there is rejection or the onset of rejection, i.e. the trend of the heart condition in terms of rejection. If the indication is positive, i.e. rejection exists, then suitable treatment is carried out as indicated at 44. Such treatment following the diagnosis of rejection may comprise giving the patient intravenous methylprednisolone for three days.

This series of steps is suitably carried out regularly over a period of time following heart transplant, e.g. when the patient remains in intensive care, or even thereafter. Preferably, the method is also carried out whenever a biopsy is performed.

Figure 3:
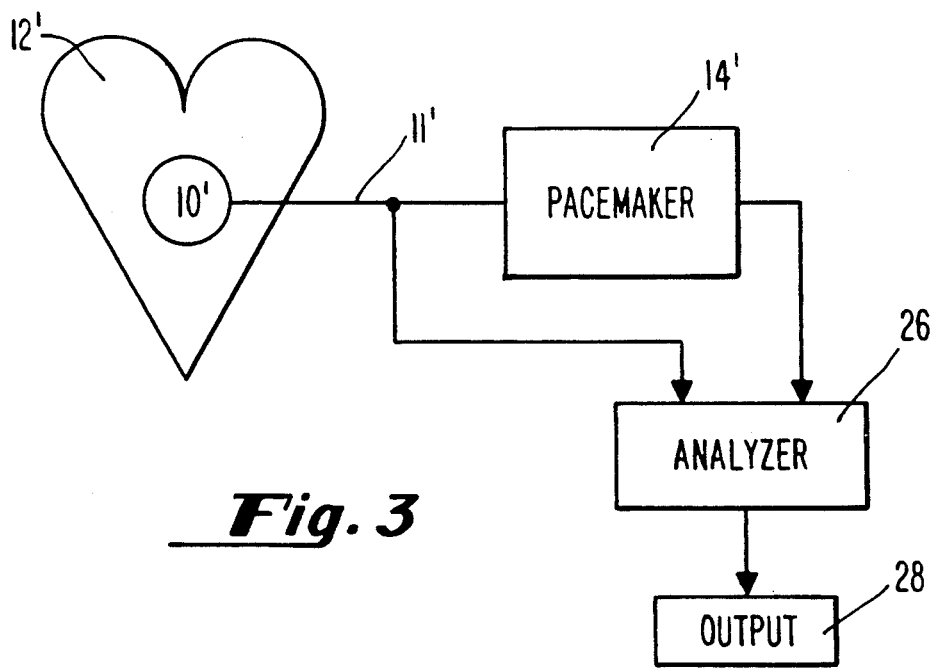
FIG. 3 is a block diagram showing another embodiment of a system for practicing the present invention.

According to another embodiment of the invention illustrated in FIG. 3, the lead 11' and electrode 10' are implanted in the heart 12, as before (epicardial or endocardial), but the pacemaker 14, is external, i.e., not implanted. In this embodiment, the pacemaker 14, may provide the heartbeat signal, including any stimulus, to an analyzer 26. The analyzer measures T-wave amplitude (or one or more of the other characteristics described below) and provides data indicative thereof to an output circuit 28. Alternatively, the analyzer 26 may be coupled to the lead 10' (as shown by the dotted line) and the analyzer may obtain the heartbeat signal directly so as to measure the T-wave amplitude (or one or more of the other characteristics described below). Thus, the pacemaker 14' need not be a T-wave sensing pacemaker as in the case of the implantable embodiment of FIG. 1 and may thus be operated externally to evoke a heartbeat. The analyzer may be a model TP2 available from the assignee of this application. The output circuit 28 may be a CRT, recorder or data storage device.

Figure 4:
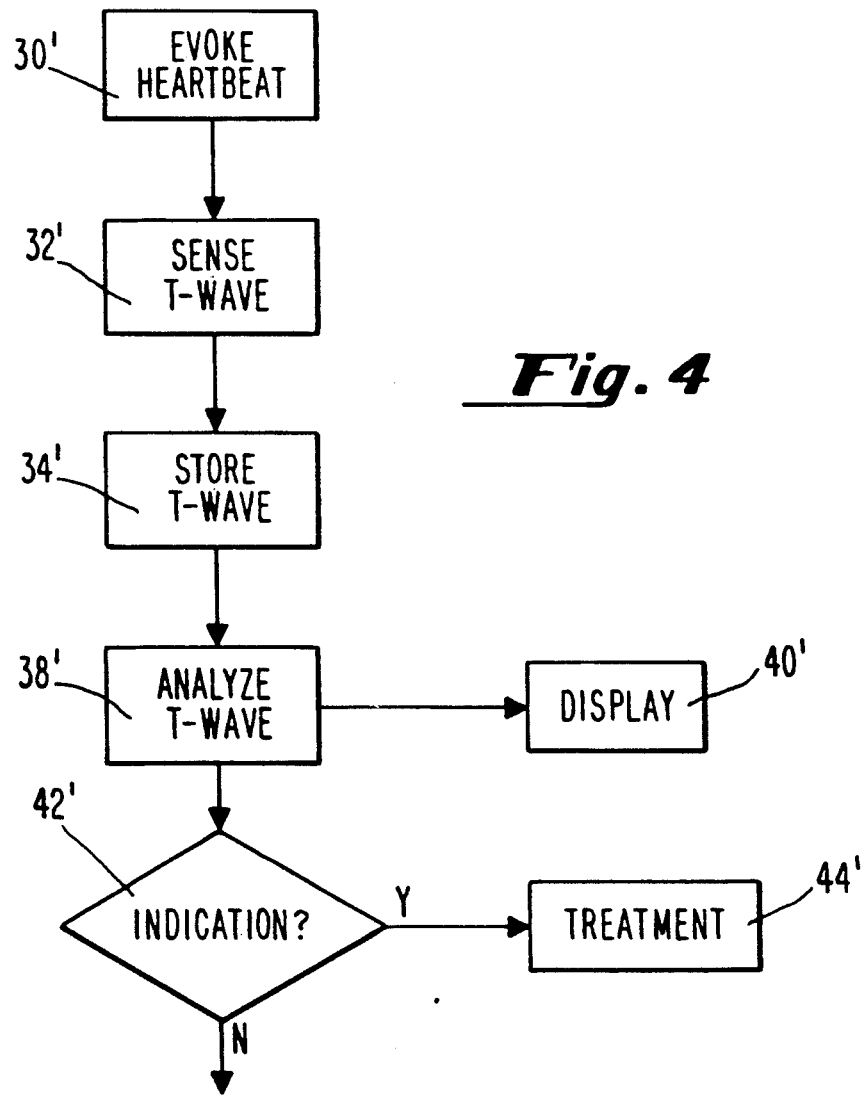
FIG. 4 is a simplified flow chart indicating a method for employing the system of FIG. 3.

FIG. 4 illustrates one method of employing the embodiment of the invention illustrated in FIG. 3. As before, the method is carried is carried out by evoking a heartbeat, as indicated at 30'. The T-wave is then sensed as indicated at 32' and then stored, e.g., in the analyzer 26, as shown at 34'. The T-wave amplitude (or one or more of the other characteristics described below) is then analyzed as shown at 38'. As before, the analysis step may include manipulation of the amplitude data, e.g., averaging or the like. The T-wave amplitude ((or one or more of the other characteristics described below) may be displayed in real time as indicated at 40'. This series of steps is suitably carried out periodically over a period of time for at least a portion of each day following heart transplant, e.g., when the patient remains in intensive care or at times when a biopsy is taken. At block 42' it is determined whether the T-wave data is significant in terms of providing an indication of whether or not there is rejection or the onset of rejection, i.e., the trend of the heart condition in terms of rejection. If the indication is positive, i.e., rejection exists, then suitable treatment is carried out as indicated at 36. The treatment may be as described previously.

The method of this invention carried out by a team at the Cardiac Transplant Research Unit, Papworth Hospital, Cambridge, UK. A modified Vitatron Rhythmyx 501 analysis system was attached to a temporary epicardial electrode for serial monitoring of patients following transplantation. Twelve patients were followed for a median of 20 days (range 3-26). Five rejection episodes were suspected clinically and treated with intravenous methylprednisolone. Right ventricular endomyocardial biopsy evidence of rejection was obtained in all cases. Each clinically suspected rejection episode was preceded by a significant and sustained fall in the evoked T-wave amplitude from a median 1.4 mV (range 1.0-2.2 mV) to 0.7 mV (range 0.5-1.0 mV). In each case, the diminution of evoked T-wave amplitude occurred prior to any other indicator of rejection. Following three days intravenous methylprednisolone, evoked T-wave amplitude increased to a median of 1.2 mV (range 0.9-1.4 mV). No fall in evoked T-wave amplitude occurred in the absence of rejection.

In another study, an external Rhythmyx pacemaker system telemetered to a TP2 analyzer was employed. Thirteen patients (12 male, 1 female), median age 49 (range 34-57) were followed for 19 (14-26) days after transplantation. Rejection was defined on endomyocardial biopsy. During the study period, 18 of the 31 biopsies performed showed evidence of rejection. One patient had no biopsies showing rejection, 7 had 1, 4 had 2, and 1 patient had 3. Following the diagnosis of rejection, patients received intravenous methylprednisone for 3 days. In 11 patients, the initial rejection episode was associated with a significant fall in the evoked T-wave amplitude from 1.3 (range 0.7-2.3) mV to 0.6 (range 0.5-1.8) mV, p less than 0.005) which began 2 (range 1-4) days earlier. One patient with uncontrolled diabetes had no change in T-wave amplitude during the rejection episode. No fall in T-wave amplitude occured in the absence of rejection. In the patients with a negative subsequent biopsy, there was an increase in T-wave amplitude to approach baseline (1.0 (range 0.7-1.8) mV). Patients with more than 1 positive biopsy had no further significant change in T-wave amplitude, which may be due to the ongoing rejection.

It is to be understood that the method of this invention may be practiced using any suitable pacemaker system and analyzer devices or equipment. The treatment utilized is, of course, a subject of physician judgment. While results to date indicate that serial monitoring of evoked T-wave amplitude using a modified Q-T sensing pacemaker is a useful and applicable noninvasive method of detecting cardiac allograft rejection, further analysis of the T-Wave morphology may be undertaken within the scope of this invention to aid in accurate diagnosis. Thus, further computer processing of T-wave data may be undertaken for determining either onset of rejection, degree of rejection, or for suggesting the optimal type of responsive treatment.

While in the preferred embodiment of this invention the amplitude of the T-wave is taken as the variable for diagnosis, it is to be understood that other characteristics of the T-wave may also be similarly analyzed, i.e., other features of the shape of the T-wave such as width or time response, or the timing of the T-wave relative to the stimulus or the R portion of the heartbeat.

Figure 5:
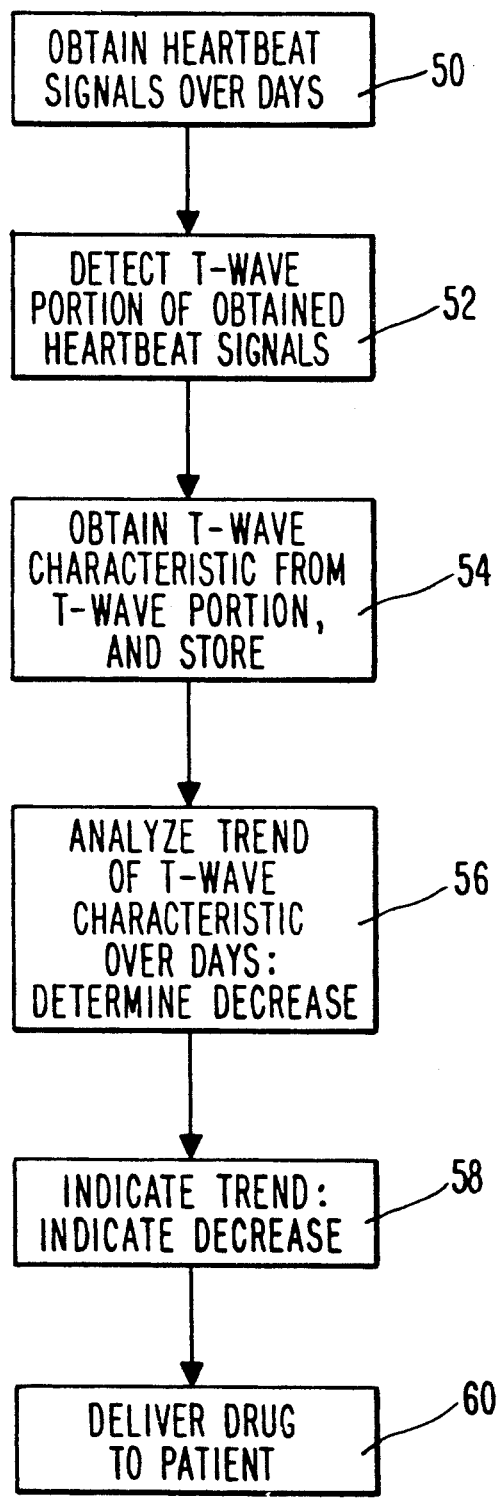
FIG. 5 is a simplified flow diagram illustrating the method of determining the tread of the (T-wave) characteristic over time and indicating when there has been a decrease in such characteristics.

The above procedures are further illustrated in FIG. 5. In practicing the method of this invention heartbeat signals are obtained, as shown at 50, following heart transplantation of the patient. As mentioned above, these signals are obtained for at least a portion of each day following heart transplant, over a number of days. The T-wave portion of the heart wave signals is detected as indicated at block 52, and a T-wave characteristic from the detected T-wave portion is obtained and stored, as indicated at 54. The T-wave characteristic may be T-wave amplitude; Q-T interval; or T-wave morphology. Thus, over the period of time following heart transplant, data is accumulated in the form of stored T-wave characteristic data. Over the same period of time, the T-wave characteristic data is analyzed, as indicated at 56, to determine the trend. As stated above, a preferred form of the method of this invention is to analyzed the trend of T-wave amplitude over a period of days following heart transplant, and determine whether it has decreased. If it is determined that T-wave amplitude has decreased over this period of time, then such a decrease is indicated, at block 58. Following an indication of T-wave amplitude decrease, treatment is accomplished by delivering an appropriate drug to the patient, as shown at 60.

Moreover, while the invention has been described as employing the evoked T-wave, it should be understood that the scope of the invention is not so limited. It is believed that the phenomena described above will be exhibited irrespective of whether the T-wave is the result of an atrial or ventricular stimulus (i.e., evoked) or the result of a spontaneous event. Thus, where spontaneous heartbeats are occurring, step 30 as shown in FIG. 3 is bypassed, as is well known, for any demand pacer of conventional design. In this case, the spontaneous T-wave is simply sensed at step 32 each heart cycle.

Still further, it is believed that all Q-T phenomena, such as amplitude, frequency, timing, morphology, Q-T interval, etc. of either the Q or T waves, or both, whether spontaneous or evoked, bear a relationship to the existence or onset of rejection, and thus may be employed as herein described to diagnose rejection. Some studies indicate that the QRS itself may contain data indicative of rejection, i.e., amplitude, frequency, morphology, and other studies indicate that the interval from an atrial or ventricular stimulus to the peak evoked R wave may contain data indicative of rejection. Obvious modifications to the apparatuses and methods described herein may be made to measure and employ these characteristics of the heartbeat signal and provide an indication of rejection. Thus, the present invention is not limited to any one of these except as may be specified in the appended claims.

The present invention has also been described as having principal application to diagnosing rejection. However, it has also been observed that the Q-T interval, as well as the other characteristics of the heartbeat signal described above, are affected by certain drugs. See, e.g., Donaldson, R.M. and Rickards, A.F., "Evaluation of Drug Induced Myocardial Repolarization Using the Paced Evoked Response", B. Heart J., 48:381 (1982). See also Becht, et al. Einfluss von Mexiletin auf die Repolarisationsphase bei Patienten mit frequenzadaptierenden TX-Schrittmachern, Herzschrittmacher 7; 164–167 (1987); Birkhead JS, et al. Heart Rate and QT Interval in Subjects Adapted to Beta-Blockade: Bradycardia and Hypotension as Uncorrelated Adaptions. Cardiovascular Research. 17; 649–655 (1983); Browne KF, et al. Prolongation of the QT Interval in Man During Sleep. Am. J. Cardil. 52; 55–59 (1983); Cobbe SM, et al. A Comparison of the Long Term Effects of Sotalol and Atenolol on QT Interval and Rhythmias after Myocardial Infarction. European Heart Journal 9; 24–31 (1988); Fnanapazir L, et al. Reliability of the Evoked Response in Determining the Paced Ventricular Rate and Performance of the QT or Rate Responsive (TX) Pacemaker, Pace 8, 5;701-714 (1985); Folgering HTM, et al. Metabolic Aspects of Maximal Exercise Performance After Slow Release Metoprolol and After Atenolol. European J Clin Pharmacol, 23; 283–288 (1982); Kevin F, et al. Modulation of the QT Interval By Autonomic Vervous System. Pace 8; 1050–1058 (1983); Kocovic D, et al. Cicadian Variations of Slim T Interval and Their Correlation With Sinus Rhythm Pace 10, 3; 700 (1987); Mandecki T, et al. Effects of Exercise and Propranold on QT Interval During Cardiac Pacing. Vitatron Actueli (Torremolinos). 71 (1985); Winter UJ, et al. Problems With the Slope Adjustment and Rate Adaption in Rate Responsive Pacemakers; Oscillation Phenomena and Sudden Rate Jumps. Cardiac Pacemakers. Ed: Behrenbeck DW, Sowton E, Fontaine G, Winter UJ. Steinkoph Verlag Darmstadt (1985); Yasuno M, et al. Clinical Experience With a New Rate-Responsive TX Pacemaker. Angiology, 1; 888–895 (1986); Zegelman M, et al. Effects of Antiarhythmic Drugs on the Stimulus T Interval and the, Rate Response of QT Related Pacemakers. Herzschrittmacher, Originalially 7; 191–195 (1987); Zegelman M, et al. Rate Responsive Pacemakers - Advantages and Weak Points In Progress in Clinical Pacing Ed Santini M, Pistolese M, Allegro A. Rome (1986).

There is a measurable relationship between the efficacy of some drugs and their influence upon one or more of these characteristics. Thus, the invention may also be employed to determine the efficacy of one or more drugs, or to determine the need for administration and/or dosage of one or more drugs. It is contemplated that the apparatus of either FIGS. 1 or 3 could be coupled to a control system for effecting a result dictated by the measured characteristic. For example, the apparatus of either FIG. 1 or 3 could be coupled via an appropriate control system to an automatic drug dispensing system which in turn is coupled to the patient for automatic administration of one or more drugs as indicated by one or more of the measured characteristics discussed above. Alternatively, the apparatus of either FIG. 1 or 3 could be coupled via a control system to one or more other life sustaining devices coupled to the patient, such as an infusion pump, that is operable as indicated by one or more of the measured conditions discussed above. All of the foregoing are contemplated as being within the scope of the present invention.

I claim:

1. A method of diagnosis of cardiac allograft rejection comprising:
   a) coupling a lead to a patient's heart, and obtaining heartbeat signals from said leads;
   (b) analyzing selected portions of the heartbeat signals, which portions include T-waves, and determining at least one characteristic of said T-waves;
   (c) determining from the characteristic the status of cardiac allograft rejection in the patient.

2. Method according to claim 1, comprising obtaining spontaneous heartbeat signals and analyzing the T-wave portions thereof.

3. Method according to claim 1 further comprising the step of pacing the patient's heart with a stimulus provided by a pacemaker coupled to the implanted lead to evoke a responsive heartbeat, and wherein the selected portions of the heartbeat signal are evoked signals.

4. Method according to claim 3 comprising implanting said pacemaker within the patient, storing data indicative of the selected portion in the pacemaker and retrieving said data upon demand by telemetry for said analyzing step.

5. Method according claim 1 wherein said analyzing step comprises determining the amplitude of the T-wave portion.

6. Method according to claim 5 further comprising carrying out said amplitude determining step over a range of 1-4 days, and determining when said amplitude has decreased over said range of days.

7. Method according to claim 1 wherein the analyzing step comprises also selecting a Q portion of the heartbeat signal and the characteristic is Q-T time interval.

8. Method according to claim 1 further comprising the step of pacing the patient's heart with stimulus pulses to evoke responsive heartbeats, and wherein said selected portions include evoked T-wave signals.

9. Method according to claim 1 further comprising the step of pacing the patient's heart with stimulus pulses to evoke responsive heartbeats, and wherein said determining step comprises determining the amplitude of the evoked T-waves.

10. Method according to claim 9, wherein said determining step further comprises determining when said T-wave amplitudes decrease over a period of at least a day.

11. A method of noninvasive diagnosis of cardiac allograft rejection comprising the steps of:
    pacing a patient's transplanted heart to evoke responsive heartbeats;
    obtaining signals of said evoked heartbeats having detectable T-wave portions; and
    analyzing at least one characteristic of said T-wave portions and determining therefrom the status of cardiac allograft rejection in said patient.

12. Method as described in claim 11 comprising carrying out said pacing over at least a predetermined period of time for a plurality of consecutive days following transplantation of the patient's heart.

13. Method as described in claim 11 wherein said T-wave characteristic is the T-wave amplitude.

14. Method of claim 13 wherein said analyzing step comprises detecting decreases in said T-wave amplitude and determining when said T-wave amplitude decreases over a period of days following transplant of the patient's heart.

15. Method as described in claim 11 comprising detecting the morphology of the T-wave and deriving said T-wave characteristic from said detected morphology.

16. Method of claim 11 further comprising the step of selecting a preferred treatment following diagnosis of cardiac allograft rejection, and carrying out said treatment on said patient.

17. A system for noninvasive acquisition of data for diagnosis of cardiac allograft rejection, comprising
    pacemaker means for delivering stimulus pulses to a patient's heart and sensing means for sensing T-waves evoked in response to said stimulus pulses, and means for receiving said evoked T-waves and providing signals representative of a characteristic thereof;
    further characterized by means for analyzing said representative signals over a period of time and outputting an indication of the trend with time of such T-wave characteristic.

18. System according to claim 17 wherein said characteristic is T-wave amplitude.

19. A method of noninvasive diagnosis of cardiac allograft rejection in a patient comprising:
    (a) evoking heartbeats in the heart of said patient over a period of at least a day;
    (b) sensing T-wave portions of said evoked heartbeats;
    (c) obtaining from said sensed T-wave portions amplitude data indicative of the amplitudes of said sensed T-waves; and
    (d) determining when said T-wave amplitude data indicates a decrease of T-wave amplitudes over a period of at least a day, thereby providing a positive indication of rejection.

20. Method according to claim 19 comprising delivering a drug to said patient following a positive indication of rejection.

* * * * *